US00PP30323P2

(12) United States Plant Patent
Olesen

(10) Patent No.: US PP30,323 P2
(45) Date of Patent: Apr. 2, 2019

(54) FLORIBUNDA ROSE PLANT NAMED 'POULNAP007'

(50) Latin Name: ***Rosa* hybrid**
Varietal Denomination: Poulnap007

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 10 days.

(21) Appl. No.: 15/731,982

(22) Filed: Sep. 5, 2017

(51) Int. Cl.
*A01H 5/02* (2018.01)

(52) U.S. Cl.
USPC ..... Plt./146
CPC ..... *A01H 5/02* (2013.01)

(58) Field of Classification Search
USPC ..... Plt./146
See application file for complete search history.

*Primary Examiner* — Anne Marie Grunberg

(57) ABSTRACT

A new garden rose plant of the Floribunda class which has abundant, orange blend flowers and attractive foliage. This new and distinct variety has shown to be uniform and stable in the resulting generations from asexual propagation.

3 Drawing Sheets

Botanical designation: *Rosa* hybrid.
Variety denomination: 'Poulnap007'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2007 and the resulting seeds were planted in a controlled environment in Fredensborg, Denmark. The new variety, named 'Poulnap007', originated as a single seedling from the stated cross The new variety may be distinguished from its male pollen parent and female seed parent primarily by the following characteristics. The male pollen parent plant has an overall growth height of 45 cm, while the new variety has an overall height of 70 cm. The female seed parent plant has yellow flowers while the new variety has orange blend flowers.

The objective of the hybridization of this rose variety was to create a new and distinct variety with unique qualities, such as:

1. Uniform and abundant orange blend flowers;
2. Continuous blooming;
3. Vigorous, but compact growth when propagated on its own roots;
4. Exceptional disease resistance.

This combination of qualities is not present in previously available commercial cultivars of this type, known to the inventor, and distinguish 'Poulnap007' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poulnap007' was selected in the spring of 2008 by the inventor as a single plant from the progeny of the aforementioned hybridization.

Asexual reproduction of 'Poulnap007' by rooted cuttings was first done by Mogens N. Olesen in the nursery in Fredensborg, Denmark in July, 2008. This initial and other subsequent asexual propagations conducted in controlled environments have demonstrated that the characteristics of 'Poulnap007' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulnap007'.

Specifically illustrated in FIG. 1 of the drawings is an open flower.

Figure 1:
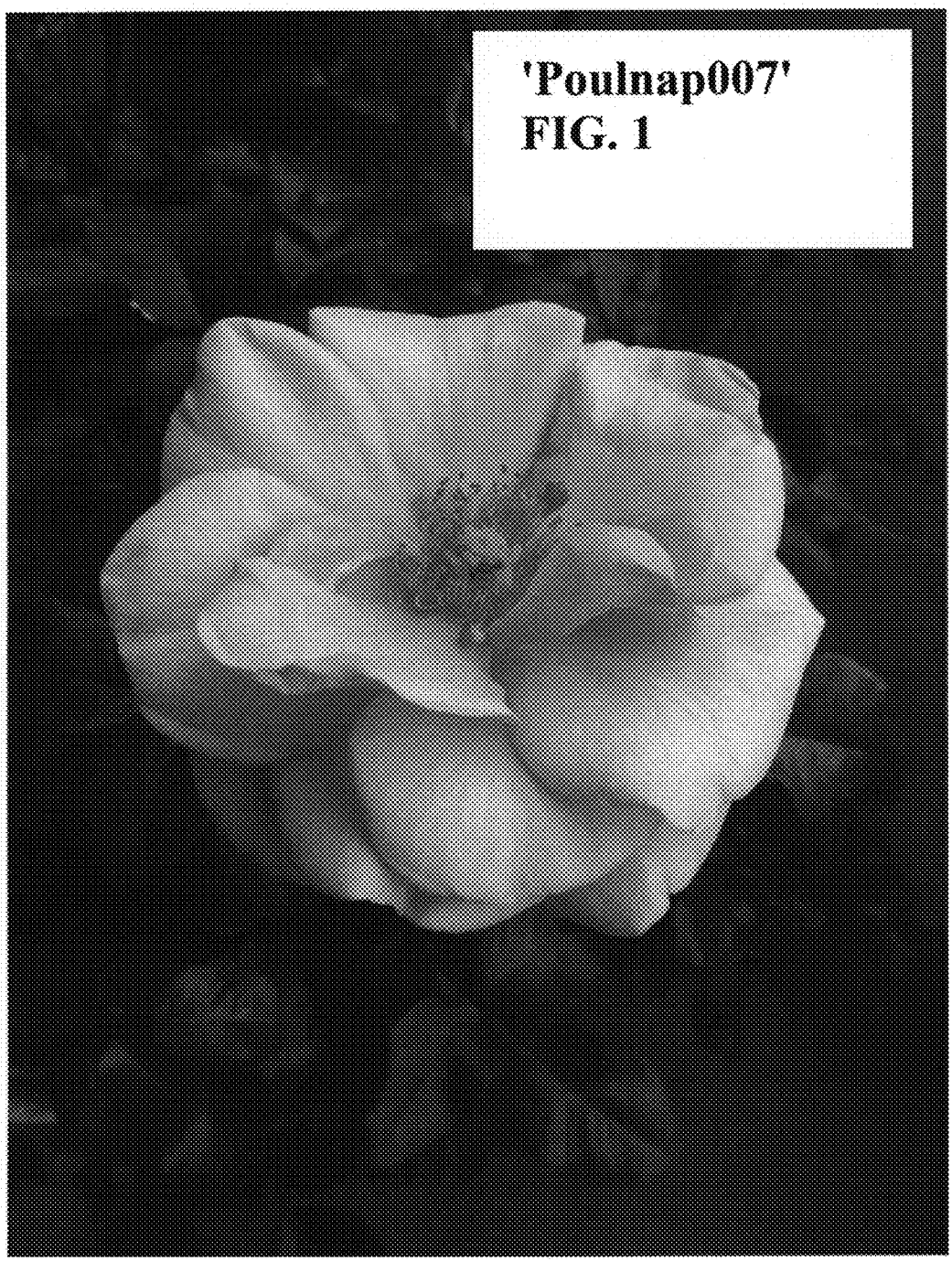
Figure 2:
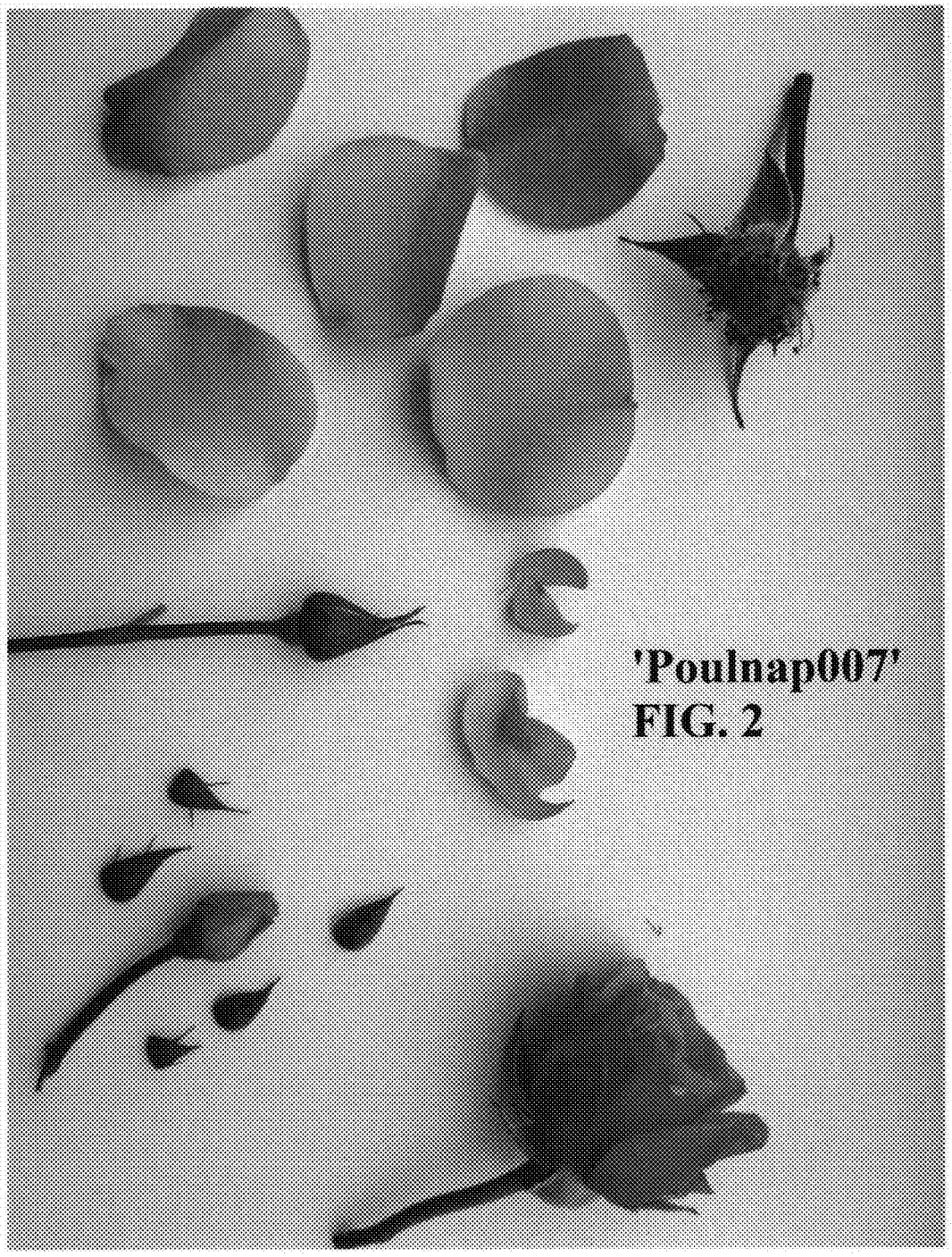

Shown in FIG. 2 are petals detached, flower bud, side view of open flower, and sepals detached, showing reproductive flower parts.

Figure 3:
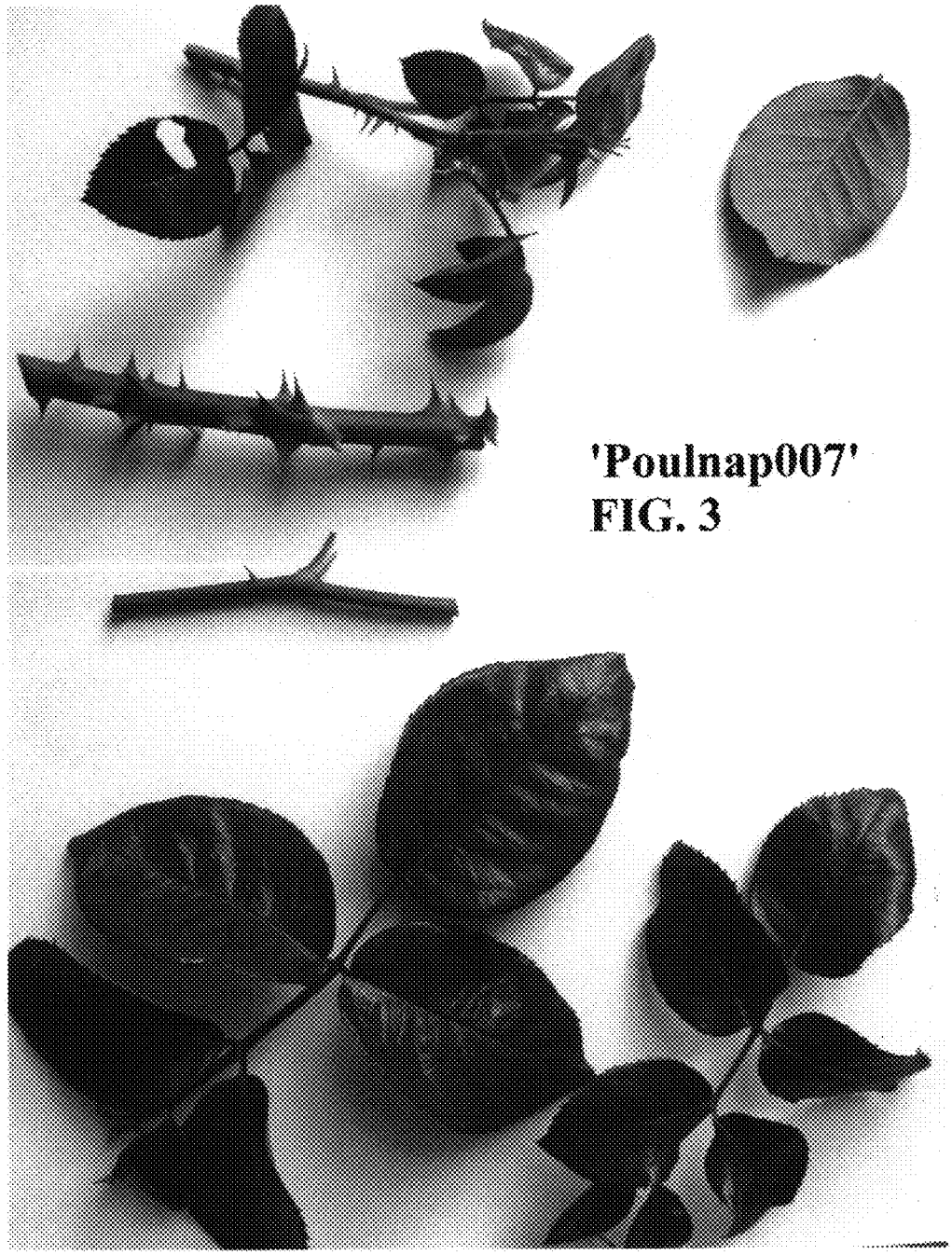

FIG. 3 shows juvenile and mature leaves and bare stems. Plants shown are 2 years of age.

DETAILED DESCRIPTION OF THE VARIETY

The following is a description of 'Poulnap007', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulfl003', U.S. Plant Pat. No. 16,552 are compared to 'Poulnap007' in Chart 1.

CHART 1

| | 'Poulnap007' | 'Poulfl003' |
|---|---|---|
| Petal Count | 30 | 55 to 60 |
| Flower Diameter | 90 to 110 mm | 70 to 75 mm |
| General Tonality of Flower Color | Yellow-Orange Group 19A | Yellow-Orange Group 18A with intonations of Orange Group 24B and 24C toward the center |

FLOWER AND FLOWER BUD

Blooming habit: Continuous.

Flower bud:

*Size.*—Upon opening, 30 mm in length from base of receptacle to end of bud. Bud diameter is 14 mm.

*Bud form.*—Ovoid.

*Bud color.*—As sepals divide petals are Orange Group 25C.

*Sepal inner surface.*—Color: Green Group 138C. Surface: Lightly pubescent.

*Sepal outer surface.*—Color: Yellow-Green Group 146B with intonations of Red-Purple Group 59A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—20 mm long, by 8 mm wide.

*Receptacle.*—Texture: Smooth. Size: 5 mm in height, 6 mm wide. Color: Yellow-Green Group 144A. Shape: Campanulate.

*Pedicel.*—Surface: Smooth, with a few stipitate glands. Length: 40 to 90 mm. Diameter: 2 to 4 mm. Color: Yellow-Green Group 144A with intonations of Greyed-Red Group 178A. Strength: Strong.

Flower bud development: Flower buds are borne in clusters of 1 to 3 flower buds per stem.

Flower bloom:

*Fragrance.*—Moderate.

*Duration.*—The blooms have a duration on the plant of approximately 10 days. Petals fall cleanly away from plant after flowers have fully matured.

*Size.*—Flower diameter is 90 to 110 mm when open. Flower depth is about 30 mm.

*Flower shape.*—Semi double, with a high pointed center which fully opens.

*Shape of flower, side view.*—The upper portion is flat. The lower portion is flat.

Petalage: Under normal conditions, flowers have about 30 petals.

General tonality of flower: Open flowers are Yellow-Orange Group 19A.

Petal color:

*Upon opening, outer petals.*—Upper surface: Orange Group 25B. Lower surface: Orange Red Group 35A.

*Upon opening, inner petals.*—Upper surface: Yellow-Orange Group 23B. Lower surface: Orange Red Group 35A.

*Basal petal spots.*—No distinctive coloration at the petal base observed.

*After opening, outer petals.*—Upper surface: Yellow-Orange Group 18A. Lower surface: Red Group 39B.

*After opening, inner petals.*—Upper surface: Yellow-Orange Group 18A. Lower surface: Red Group 39B.

Petals:

*Petal reflex.*—Somewhat reflexed bilaterally.

*Margin.*—Entire and uniform. Occasionally a cleft in the margin apex. Moderate undulations.

*Shape.*—Broad and elliptic. Apex shape: Rounded. Base shape: Acute and obtuse.

*Size.*—50 mm (l) by 50 mm (w).

*Texture.*—Smooth.

*Thickness.*—Average.

Petaloids:

*Size.*—20 mm (l) by 10 mm (w).

*Quantity.*—About 5.

*Shape.*—Irregular.

*Color.*—Upper surface is Yellow-Orange Group 18A. Lower surface is Red Group 39B.

Reproductive flower parts:

*Pollen.*—None observed.

*Anthers.*—Size: 2 mm in length. Color: Yellow-Orange Group 20A. Quantity: 120 on average.

*Filaments.*—Color: Yellow-Orange Group 22A. Length: 7 to 12 mm.

*Pistils.*—Length: 3 mm. Quantity: 50 on average.

*Stigmas.*—Color: Yellow-Orange Group 22B.

*Styles.*—Color: Orange-Red Group 34A.

*Location of stigmas.*—Inferior in location relative to the length of the filaments and the height of the anthers.

*Hips.*—None Observed.

PLANT

Plant growth: Upright and bushy. Plants are about 70 cm in height, and 60 cm wide.

Stems:

*Color of juvenile growth.*—Yellow-Green Group 144B.

*Color of mature growth.*—Yellow-Green Group 144A.

*Length.*—Canes are about 40 cm from the base of the plant to the flowering portion.

*Diameter.*—About 10 mm.

*Internodes.*—On mature canes about 65 mm between nodes.

*Surface texture.*—Young wood: Smooth. Older wood: Smooth.

Long prickles:

*Incidence.*—20 prickles per 10 cm of stem.

*Size.*—Average length of prickles on mature stems is 8 mm.

*Shape.*—Upper portion is linear. Lower portion is concave.

*Color.*—Juvenile prickles: Greyed-Red Group 179B with intonations of Yellow-Green Group 144C at base. Mature prickles: Greyed-Red Group 179B.

Plant foliage:

*Compound leaf.*—About 170 mm (l)×145 (w).

*Quantity.*—1 leaf per 10 cm of stem on average.

*Leaf bearing angle to the stem.*—45 degrees.

*Color of juvenile foliage.*—Upper side: Yellow-Green Group 144A with marginal intonations of Greyed-Red Group 179A. Lower side: Greyed-Red Group 179A.

*Color of mature foliage.*—Upper side: Yellow-Green Group 147A. Lower side: Yellow-Green Group 147C.

Plant leaves and leaflets:

*Stipules*.—Size: 25 mm long, 5 mm wide. Quantity: 2 per compound leaf. Shape: Linear, slightly broad based with outward extending apices. Margins: Finely serrated. Color: Yellow-Green Group 144A.

*Petiole*.—Length: About 20 mm. Diameter: 2 mm. Upper surface color: Yellow-Green Group 146A. Lower surface color: Yellow-Green Group 144A.

*Rachis*.—Length: About 30 mm. Upper surface color: Yellow-Green Group 146A with some leaves showing anthocyanin the color of Greyed-Red Group 178B. Lower surface color: Yellow-Green Group 144A.

*Leaflet*.—Quantity: Normally 5 leaflets. Margins: Serrated. Size: Terminal leaflets are about 80 mm long, 60 mm wide. Shape: Generally ovate. Base: Rounded. Apex: Acuminate. Texture: Smooth. Thickness: Average. Arrangement: Odd pinnate. Venation: Reticulate. Glossiness: Very glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Floribunda rose class named 'Poulnap007', substantially as illustrated and described herein, due to its abundant orange blend flowers, disease resistance, and extended period of bloom.

* * * * *

'Poulnap007'

'Poulnap007'

'Poulnap007'